United States Patent [19]

Sanders et al.

[11] Patent Number: 5,433,193

[45] Date of Patent: * Jul. 18, 1995

[54] BREATHING GAS DELIVERY METHOD AND APPARATUS

[75] Inventors: Mark H. Sanders, Wexford; Ronald J. Zdrojkowski, Pittsburgh, both of Pa.

[73] Assignee: Respironics Inc., Murrysville, Pa.

[*] Notice: The portion of the term of this patent subsequent to Sep. 22, 2009 has been disclaimed.

[21] Appl. No.: 947,156

[22] Filed: Sep. 18, 1992

Related U.S. Application Data

[63] Continuation-in-part of Ser. No. 411,012, Sep. 22, 1989, Pat. No. 5,148,802.

[51] Int. Cl.$^6$ ............................................. A61M 16/00
[52] U.S. Cl. ........................... 128/204.18; 128/204.21; 128/204.23
[58] Field of Search ................ 128/204.18, 204.21, 128/204.23

[56] References Cited

U.S. PATENT DOCUMENTS

| | | | |
|---|---|---|---|
| 3,191,596 | 6/1965 | Bird et al. ......................... | 128/29 |
| 3,267,935 | 8/1966 | Andreasan et al. ................. | 128/29 |
| 3,362,404 | 1/1968 | Beasley ............................ | 128/145 |
| 3,485,243 | 12/1969 | Bird et al. ....................... | 128/204.25 |
| 3,580,051 | 5/1971 | Blevins ............................ | 73/40 |
| 3,669,108 | 6/1972 | Sundblum et al. ................. | 128/145 |
| 3,741,208 | 6/1973 | Jonsson et al. ................... | 128/204.21 |
| 3,896,800 | 7/1975 | Cibulka ........................... | 128/145 |
| 3,961,627 | 6/1976 | Ernst et al. ...................... | 128/204.21 |
| 3,972,327 | 8/1976 | Ernst et al. ...................... | 128/145.8 |
| 4,031,885 | 6/1977 | Davis et al. ...................... | 128/2.08 |
| 4,036,221 | 7/1977 | Hillsman et al. ................... | 128/204.23 |
| 4,050,458 | 9/1977 | Friend ............................. | 128/145.8 |
| 4,082,093 | 4/1978 | Fry et al. ......................... | 128/142 |
| 4,207,884 | 6/1980 | Isaacson .......................... | 128/200 |
| 4,323,064 | 4/1982 | Hoenig et al. ..................... | 128/204 |
| 4,421,113 | 12/1983 | Gedeon et al. .................... | 128/204.23 |
| 4,457,303 | 7/1984 | Durkan ............................ | 128/202.24 |
| 4,506,666 | 3/1985 | Durkan ............................ | 128/204.23 |
| 4,519,388 | 5/1985 | Schwandbin et al. .............. | 128/204.25 |
| 4,527,557 | 7/1985 | Devries et al. ................... | 128/204.23 |
| 4,535,766 | 8/1985 | Baum ............................... | 128/204.23 |
| 4,539,984 | 9/1985 | Kiszel et al. ..................... | 128/204.23 |
| 4,550,726 | 11/1985 | McEwen .......................... | 128/202.22 |
| 4,567,888 | 2/1986 | Robert et al. ..................... | 128/204.21 |
| 4,570,631 | 2/1986 | Durkan ............................ | 128/204.23 |
| 4,584,996 | 4/1986 | Blum .............................. | 128/204.21 |
| 4,592,349 | 6/1986 | Bird ................................ | 128/204 |
| 4,612,928 | 9/1986 | Tiep et al. ........................ | 128/204.23 |
| 4,635,631 | 1/1987 | Izumi .............................. | 128/204.21 |
| 4,637,385 | 1/1987 | Rusz ............................... | 128/204.21 |
| 4,655,213 | 4/1987 | Rapoport et al. ................. | 128/205.25 |
| 4,667,669 | 5/1987 | Pasternak ........................ | 128/204 |
| 4,686,974 | 8/1987 | Sato et al. ........................ | 128/204.23 |
| 4,686,975 | 8/1987 | Naimon et al. ................... | 128/204.23 |
| 4,773,411 | 9/1988 | Downs ............................ | 128/204.18 |
| 4,776,333 | 10/1988 | Miyamae .......................... | 128/204.21 |
| 4,782,832 | 11/1988 | Trimble et al. .................... | 128/207 |

(List continued on next page.)

FOREIGN PATENT DOCUMENTS

| | | |
|---|---|---|
| 484764 | 5/1976 | Australia . |
| 83901/82 | 11/1982 | Australia . |
| 183901 | 11/1982 | Australia . |
| 560885 | 4/1985 | Australia . |
| 615956 | 5/1989 | Australia . |
| 0274996 | 7/1988 | European Pat. Off. . |
| 1583273 | 1/1981 | United Kingdom . |
| 2054387 | 2/1981 | United Kingdom . |
| WO/8905669 | 6/1989 | WIPO . |

OTHER PUBLICATIONS

Black, J. Waylon and Grover, Bruce S., *A Hazard of Pressure Support Ventilation*, Feb., 1988 Chest.

*Effects on the Work of Breathing & Flow Triggering Versss Pressure Triggering* Puritan Bennett.

(List continued on next page.)

Primary Examiner—Edgar S. Burr
Assistant Examiner—Aaron J. Lewis
Attorney, Agent, or Firm—J. Stewart Brams

[57] ABSTRACT

An improved methodology and apparatus for delivery of breathing gas such as fop the treatment of sleep apnea through application of alternating high and low level positive airway pressure within the airway of the patient with the high and low airway pressure being coordinated with the spontaneous respiration of the patient.

64 Claims, 5 Drawing Sheets

U.S. PATENT DOCUMENTS

| | | | |
|---|---|---|---|
| 4,802,485 | 2/1989 | Bowers et al. | 128/633 |
| 4,807,616 | 2/1989 | Adahan | 128/204.21 |
| 4,823,787 | 4/1989 | Adahan | 128/203.27 |
| 4,823,788 | 4/1989 | Smith et al. | 128/204.21 |
| 4,830,008 | 5/1989 | Meer | 128/721 |
| 4,877,023 | 10/1989 | Zalkin | 128/204 |
| 4,941,469 | 7/1990 | Aophan | 128/205.12 |
| 4,957,107 | 9/1990 | Sipin | 128/204.21 |
| 5,044,362 | 9/1991 | Younes | 128/204.21 |
| 5,065,756 | 11/1991 | Rapoport | 128/204.18 |
| 5,107,830 | 4/1992 | Younes | 128/204.18 |
| 5,107,831 | 4/1992 | Halpern et al. | 128/204.23 |
| 5,117,819 | 6/1992 | Servidio et al. | 128/204.18 |
| 5,134,995 | 8/1992 | Gruenke et al. | 128/204 |
| 5,148,802 | 9/1992 | Sanders et al. | 128/204.18 |
| 5,161,525 | 11/1992 | Kimm et al. | 128/204.21 |

OTHER PUBLICATIONS

Effects of Expiratory Positive Airway Pressure Ensleep Induced Respiratory Abnormalities in Patients with Hybensomnia-Sleep Apnea Syndrome—Akshay K. Mahadejia-Am. Rev. Re. 50 R.

*Reversal of Pickwickian Syndrome by Long-Term Use of Nocturnal Nasal Airway Pressure* Rapoport D. M., Sorkin B. Garay SM, Zodronic DM N. Engl J. Med 1986, 307: pp. 931–933.

*The Effects of Nasal Cpap on Various Sleep Apnea Patients* Sander M. H., Holzer A. C., Pennock B. E. Chest 1983; 841 p. 336 Mannual Meeting of American College of Chest Physicians Chicago, Ill. Oct. 1983.

*The New Generation of Mechanical Ventilators* Spearman C. S. & J. Sanders H. G., Jr/ Resp. Care Jun. 1987 vol. 32 #6.

"Flow-by Option 50" by Puritan-Bennett, Oct. 1986, pp. 1-6.

Nocturnal Positive Pressure Ventilation via Nasal Mask; G. R. Kerby, L. S. Mayer, S. K. Pingleton; American Review of Respiratory Disease, 1987, vol. 135, pp. 738–740.

Nocturnal Positive Pressure Ventilation via a Nasal Mark, C. S. Sullivan, E. R. Ellis, (letter to the Editor); N. M. T. Braun (Replay from Author) American Review of Respiratory Disease, 1987, vol. 135, pp. 791-792.

Biphasic Positive Airway Pressure (BIPAP)—*Anaesthesist* (1989) 38:451–458 M. Baum, H. Benzer, Ch. Putensen, W. Koller and G. Putz.

Treatment of Cardiorespiratory Disturbances During Sleep Interdiscipl. Topics Geront., vol. 22, pp. 47-6-7—C. E. Sullivan, F. G. Issa, E. Ellis, J. Bruderer, V. McCauley, P. T. Bye, R. Grunstein, L. Costas.

Continuous Positive Airway Pressure (CPAP) Improves Efficacy of Pressure Support (PS) Ventilation in Severe Chronic Obstructive Pulmonary Disease (COPD) Montreal General Hosp. Meakins-Christie Labs. E. Calderini, B. Petrof, S. B. Gottfried.

Noctural Ventilation—A New Method—(Norma M. T. Braun, M.D. Roosevelt Hospital—Editorial).

Nursing Photobook—Providing Respiratory Care, Nursing 83 Books Springhouse Corp., Pennsylvania pp. 122-126 Role of Sleep in the Development of Respiratory Failure in Neuromuscular Disease—P. T. Bye, E. R. Ellis, R. D. Donnelly, F. G. Iasa, C. E. Sullivan—Sleep Disorders Clinical Disorders.

Bi-Level Positive Airway Pressure (BIPAP): A Low-Cost, Simple Method of Providing Nocturnal Assisted Ventilation, D. A. Strumpf, C. C. Carlisle, R. P. Millman, N. S. Hill R. I. Hospital & Brown University.

Nocturnal Intermittent Positive Pressure Ventilation Through the Nasal Route in Sleep Apnea Syndrome Refractory to Continuous Postive Airway Pressure D. Robert D. Brunel, P. Leger, J. Larzal Press Medicine, vol. 16, No. 44, 1987 p. 2231.

Mechanical Ventilatory Support—Intensive Care Manual, Chapter 17 Statutory Declarations and curriculum vitae for E. R. Ellis, C. E. Sullivan and G. C. Grant, and Statutory Declaration for K. Daffurn.

Treatment of Alveolar Hypoventilation in a Six--Year-Old Girl with Intermittent Positive Pressure Ventilation Through a Nose Mask (Ellis, McCauley, Mellis and Sullivan).

Nasal Ventilation to Facilitate Weaning in Patients with Chronic Respiratory Insufficiency (Udwadia, Santis, Steven and Simonds).

Treatment of Respiratory Failure During Sleep in Patients with Neuromuscular Disease—Positive-Pressure Ventilation Through a Nose Mark (Ellis, Bye, Bruderer, and Sullivan).

7200a—Option #50 Flow-By-(Puritan Bennett Corp.).

Flow-By Option 50 document 20535A 10-86.

Noninvasive Ventilatory Support during Sleep Improves Respiratory Failure in Kyphoscoliosis (Ellis, Grunstein, Chan, Bye and Sullivan) Chest Oct. 1988.

(List continued on next page.)

OTHER PUBLICATIONS

Intermittent Positive Pressure Ventilation by Nasal Mask: Technique and Applications (Carroll and Brantwaite)—Intensive Care Medicine, Springer-Verlag 1988.

Control of nocturnal hypoventilation by nasal intermittent positive pressure ventilation (Carroll and Brantwaite) Thorax 1988:43;349-353.

Central Alevolar Hypoventilation and Sleep—Treatment by Intermittent Positive-Pressure Ventilation through Nasal Mask in an Adult (Guilleminault, Stoohs, Schneider, Podszus, Peter and Wichert) CHEST Nov. 1989.

Clinical investigations in critical care—Intermittent volume cycled mechanical ventilation via nasal mask in patients with respiratory failure due to COPD (W. Marino) CHEST vol. 99, pp. 681-684 Mar. 1991 issue.

Reversal of the "Pickwickian Syndrome" by long-term use of nocturnal nasal-airway pressure (Rapoport, Sorkin, Garay and Goldring) Medical Intelligence—Rapoport et al., vol. 307, No. 15.

Noninvasive nasal mask-assisted ventilation in respiratory failure of Duchenne muscular dystrophy (Segall) CHEST Jun. 1988 pp. 1298-1300.

Airway pressure release ventilation (Stock, Downs & Frolicher) Critical Care Medicine vol. 15 No. 5 pp. 462-466.

Investigation of the spontaneous modes of breathing of different ventilators (Cox, Tinloi and Farrimond) Intensive Care Med. (1988) 14-532-537.

Intermittent positive pressure ventilation via nasal access in the management of respiratory insuffiency (Bach, Alba, Mosher and Delaubier) CHEST 1992 pp. 168-170.

Added inspiratory work of breathing during CPAP ventilation: comparison of two demand-valve devices with a continuous flow-system (Viale, Annat, Percival, Bertrand and Motin) Intensive Care Med. (1986) 12-374-377.

The role of pressure support ventilation in reducing work of breathing (KACMAREK) Respiratory Care, Feb. 1988, vol. 33 No. 2 pp. 99-120.

Respiratory function during pressure support ventilation (MacIntyre) CHEST/89/5/May 1986 pp. 577-683.

Nocturnal positive pressure ventilation via nasal mask (Kerby, Mayer and Pingleton) Am Rev Respir Dis 1987;135:738-740.

Effects of expiratory positive airway pressure on sleep-induced respiratory abnormalities in patients with hypersomnia-sleep apnea syndrome (Mahadevia, Onal and Lopata) Am Rev Respir Dis 1983 128:708-711.

Assessment & treatment of nocturnal respiratory failure-new advances (Ellis) RPA Magazine Autumn 1988 pp. 13-15.

Patient Compliance with Nasal CPAP Therapy for Sleep Apnea (Sanders, Gruendl, Rogers).

Prolonged Expiratory Phase in Sleep Apnea (Sanders, Rogers & Pennock).

Nasal CPAP Effect on Patterns of Sleep Apnea (Sanders).

CPAP Via Nasal Mask: A Treatment for Occlusive Sleep Apnea (Sanders, Moore and Eveslage).

Intermittent Mandatory Ventilation (Weisman, Rinaldo, Rogers & Sanders).

BREATHING GAS DELIVERY METHOD AND APPARATUS

This is a continuation-in-part of application Ser. No. 07/411,012 filed on Sep. 22, 1989 now U.S. Pat. No. 5,148,802.

BACKGROUND OF THE INVENTION

The sleep apnea syndrome afflicts an estimated 1% to 3% of the general population and is due to episodic upper airway obstruction duping sleep, Those afflicted with sleep apnea experience sleep fragmentation and intermittent, complete or nearly complete cessation of ventilation duping sleep with potentially severe degrees of oxyhemoglobin unsaturation. These features may be translated clinically into debilitating daytime sleepiness, cardiac disphythmias, pulmonary-artery hypertension, congestive heart failure and cognitive disfunction. Other sequelae of sleep apnea include night ventricular dysfunction with cor pulmonale, carbon dioxide retention during wakefulness as well as during sleep, and continuous reduced arterial oxygen tension. Hypersomnolent sleep apnea patients may be at risk for excessive mortality from these factors as well as by an elevated risk for accidents while driving and/on operating potentially dangerous equipment.

Although details of the pathogenesis of upper airway obstruction in sleep apnea patients have not been fully defined, it is generally accepted that the mechanism includes either anatomic or functional abnormalities of the upper airway which result in increased air flow resistance. Such abnormalities may include narrowing of the upper airway due to suction forces evolved during inspiration, the effect of gravity pulling the tongue back to appose the pharyngeal wall, and/or insufficient muscle tone in the upper airway dilator muscles. It has also been hypothesized that a mechanism responsible for the known association between obesity and sleep apnea is excessive soft tissue in the anterior and lateral neck which applies sufficient pressure on internal structures to narrow the airway.

The treatment of sleep apnea has included such surgical interventions as uvalopalatopharyngoplasty, gastric surgery for obesity, and maxillo-facial reconstruction. Another mode of surgical intervention used in the treatment of sleep apnea is tracheostomy, These treatments constitute major undertakings with considerable risk of post-operative morbidity if not mortality. Pharmacologic therapy has in general been disappointing, especially in patients with mope than mild sleep apnea. In addition, side effects from the pharmacologic agents that have been used are frequent. Thus, medical practitioners continue to seek non-intrusive modes of treatment for sleep apnea with high success rates and high patient compliance including, for example in cases relating to obesity, weight loss through a regimen of exercise and regulated diet.

Recent work in the treatment of sleep apnea has included the use of continuous positive airway pressure (CPAP) to maintain the airway of the patient in a continuously open state during sleep. For example, U.S. Pat. No. 4,655,213, and Australian patent AU-B-83901/82 both disclose sleep apnea treatments based on continuous positive airway pressure applied within the airway of the patient.

Also of interest is U.S. Pat. No. 4,773,411, which discloses a method and apparatus for ventilatory treatment characterized as airway pressure release ventilation and which provides a substantially constant elevated airway pressure with periodic short term reductions of the elevated airway pressure to a pressure magnitude no less than ambient atmospheric pressure.

Publications pertaining to the application of CPAP in treatment of sleep apnea include the following:

1. Lindsay, D A, Issa F G, and Sullivan C. E. "Mechanisms of Sleep Desaturation in Chronic Airflow Limitation Studied with Nasal Continuous Positive Airway Pressure (CPAP), "*Am Rev Respir Dis,* 1982; 125: p. 112.
2. Sanders M H, Moope S E, Eveslage J. "CPAP via nasal mask: A treatment for occlusive sleep apnea," *Chest,* 1983; 83: pp. 144–145.
3. Sullivan C E, Berthon-Jones M, Issa F G. "Remission of severe obesity-hypoventilation syndrome after short-term treatment during sleep with continuous positive airway pressure," *Am Rev Respir Dis,* 1983; 128: pp. 177–181.
4. Sullivan C E, Issa F G, Berthon-Jones M, Eveslage. "Reversal of obstructive sleep apnea by continuous positive airway pressure applied through the nares," *Lancet,* 1981; 1: pp. 862–865.
5. Sullivan C E, Berthon-Jones M. Zssa F G. "Treatment of obstructive apnea with continuous positive airway pressure applied through the nose." *Am Rev Respir Dis,* 1982; 125: p. 107. Annual Meeting Abstracts.
6. Rapoport D N, Sorkin B, Garay S M, Goldring R M. "Reversal of the 'Pickwickian Syndrome' by long-term use of nocturnal nasal-airway pressure," *N Engl J. Med,* 1982; 307: pp. 931–933.
7. Sanders M H, Holzer B C, Pennock B E. "The effect of nasal CPAP on various sleep apnea patterns," *Chest,* 1983; 84: p. 336. Presented at the Annual Meeting of the American College of Chest Physicians, Chicago Ill., October 1983.

Although CPAP has been found to be very effective and well accepted, it suffers from some of the same limitations, although to a lesser degree, as do the surgery options; specifically a significant proportion of sleep apnea patients do not tolerate CPAP well. Thus, development of other viable non-invasive therapies has been a continuing objective in the art.

BRIEF SUMMARY OF THE INVENTION

The present invention contemplates a novel and improved method for treatment of sleep apnea as well as novel methodology and apparatus for carrying out such improved treatment method. The invention contemplates the treatment of sleep apnea through application of pressure at variance with ambient atmospheric pressure within the upper airway of the patient in a manner to promote dilation of the airway to thereby relieve upper airway occlusion during sleep.

In one embodiment of the invention, positive pressure is applied alternately at relatively higher and lower pressure levels within the airway of the patient so that the pressure-induced force applied to dilate the patient's airway is alternately a larger and a smaller magnitude dilating force. The higher and lower magnitude positive pressures are initiated by spontaneous patient respiration with the higher magnitude pressure being applied during inspiration and the lower magnitude pressure being applied during expiration.

The invention further contemplates a novel and improved apparatus which is operable in accordance with a novel and improved method to provide sleep apnea treatment. More specifically, a flow generator and an adjustable pressure controller supply air flow at a predetermined, adjustable pressure to the airway of a patient through a flow transducer. The flow transducer generates an output signal which is then conditioned to provide a signal proportional to the instantaneous flow rate of air to the patient. The instantaneous flow rate signal is fed to a low pass filter which passes only a signal indicative of the average flow rate over time. The average flow rate signal typically would be expected to be a value representing a positive flow as the system is likely to have at least minimal leakage from the patient circuit (e.g. small leaks about the perimeter of the respiration mask worn by the patient). The average flow signal is indicative of such leakage because the summation of all other components of flow over time must be essentially zero since inspiration flow must equal expiration flow volume over time, that is, over a period of time the volume of air breathed in equals the volume of the gases breathed out.

Both the instantaneous flow signal and the average flow rate signal are fed to an inspiration/expiration decision module which is, in its simplest form, a comparator that continually compares the input signals and provides a corresponding drive signal to the pressure controller. In general, when the instantaneous flow exceeds average flow, the patient is inhaling and the drive signal supplied to the pressure controller sets the pressure controller to deliver air, at a preselected elevated pressure, to the airway of the patient. Similarly, when the instantaneous flow rate is less than the average flow rate, the patient is exhaling and the decision circuitry thus provides a drive signal to set the pressure controller to provide a relatively lower magnitude of pressure in the airway of the patient. The patient's airway thus is maintained open by alternating higher and lower magnitudes of pressure which are applied during spontaneous inhalation and exhalation, respectively.

As has been noted, some sleep apnea patients do not tolerate standard CPAP therapy. Specifically, approximately 25% of patients cannot tolerate CPAP due to the attendant discomfort. CPAP mandates equal pressures during both inhalation and exhalation. The elevated pressure during both phases of breathing may create difficulty in exhaling and the sensation of an inflated chest. However, we have determined that although both inspiratory and expiratory air flow resistances in the airway are elevated during sleep preceding the onset of apnea, the airway flow resistance may be less during expiration than during inspiration. Thus it follows that the bi-level CPAP therapy of our invention as characterized above may be sufficient to maintain pharyngeal patency during expiration even though the pressure applied during expiration is not as high as that needed to maintain pharyngeal patency during inspiration. In addition, some patients may have increased upper airway resistance primarily during inspiration with resulting adverse physiologic consequences. Thus, our invention also contemplates applying elevated pressure only during inhalation thus eliminating the need for global (inhalation and exhalation) increases in airway pressure. The relatively lower pressure applied during expiration may in some cases approach or equal ambient pressure. The lower pressure applied in the airway during expiration enhances patient tolerance by alleviating some of the uncomfortable sensations normally associated with CPAP.

Under prior CPAP therapy, pressures as high as 15 cm $H_2O$ have been required, and some patients on nasal CPAP thus have been needlessly exposed to unnecessarily high expiratory pressures with the attendant discomfort and elevated mean airway pressure, and theoretic risk of barotrauma. Our invention permits independent application of a higher inspiratory airway pressure in conjunction with a lower expiratory airway pressure in order to provide a therapy which is better tolerated by the 25% of the patient population which does not tolerate CPAP therapy, and which may be safer in the other 75% of the patient population.

As has been noted hereinabove, the switch between higher and lower pressure magnitudes can be controlled by spontaneous patient respiration, and the patient thus is able to independently govern respiration rate and volume. As has been also noted, the invention contemplates automatic compensation for system leakage whereby nasal mask fit and air flow system integrity are of less consequence than in the prior art. In addition to the benefit of automatic leak compensation, other important benefits of the invention include lower mean airway pressures for the patient and enhanced safety, comfort and tolerance.

It is accordingly one object of the present invention to provide a novel and improved method for treatment of sleep apnea.

A further object of the invention to provide a novel and improved apparatus which is operable according to a novel methodology in carrying out such a treatment for sleep apnea.

Another object of the invention is to provide a method and apparatus for treating sleep apnea by application of alternately high and low magnitudes of pressure in the airway of the patient with the high and low pressure magnitudes being initiated by spontaneous patient respiration.

Another object of the invention is to provide an apparatus for generating alternately high and low pressure gas flow to a consumer of the gas with the higher and lower pressure flows being controlled by comparison of the instantaneous flow rate to the gas consumer with the average flow rate to the consumer, which average flow rate may include leakage from the system, and whereby the apparatus automatically compensates for system leakage.

These and other objects and further advantages of the invention will be more readily appreciated upon consideration of the following detailed description and accompanying drawings, in which.

Figure 1:
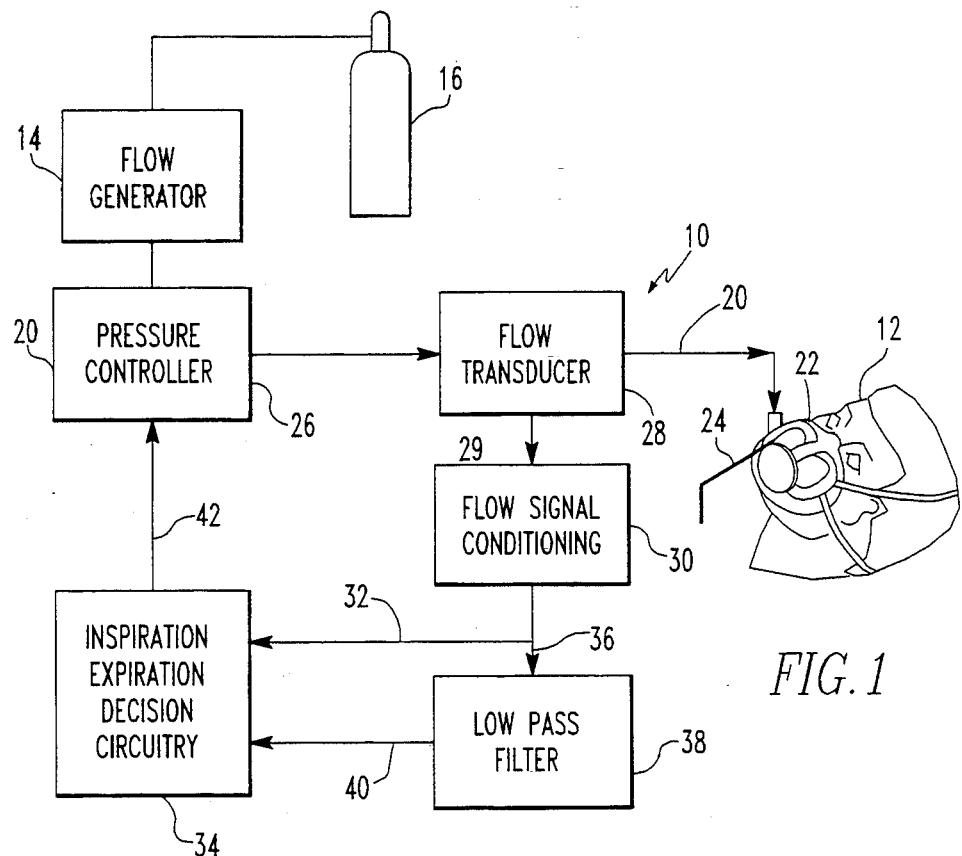
FIG. 1 is a functional block diagram of an apparatus according to the instant invention which is operable according to the method of the instant invention.

There is generally indicated at 10 in FIG. 1 an apparatus according to one presently preferred embodiment of the instant invention and shown in the form of a functional block diagram. Apparatus 10 is operable according to a novel process which is another aspect of the instant invention for delivering breathing gas such as air alternately at relatively higher and lower pressures (i.e., equal to or above ambient atmospheric pressure) to a patient 12 for treatment of the condition known as sleep apnea.

Apparatus 10 comprises a gas flow generator 14 (e.g., a blower) which receives breathing gas from any suitable source, a pressurized bottle 16 or the ambient atmosphere, for example. The gas flow from flow generator 14 is passed via a delivery conduit 20 to a breathing appliance such as a mask 22 of any suitable known construction which is worn by patient 12. The mask 22 may preferably be a nasal mask or a full face mask 22 as shown. Other breathing appliances which may be used in lieu of a mask include nasal cannulae, an endotracheal tube, or any other suitable appliance for interfacing between a source of breathing gas and a patient, consistent with the desired effect to be achieved through use of the apparatus 10.

The mask 22 includes a suitable exhaust port means, schematically indicated at 24, for exhaust of breathing gases during expiration. Exhaust port 24 preferably is a continuously open port which imposes a suitable flow resistance upon exhaust gas flow to permit a pressure controller 26, located in line with conduit 20 between flow generator 14 and mask 22, to control the pressure of air flow within conduit 20 and thus within the airway of the patient 12. For example, exhaust port 24 may be of sufficient cross-sectional flow area to sustain a continuous exhaust flow of approximately 15 liters per minute. The flow via exhaust port 24 is one component, and typically the major component of the overall system leakage, which is an important parameter of system operation. In an alternative embodiment to be discussed hereinbelow, it has been found that a non-rebreathing valve may be substituted for the continuously open port 24.

The pressure controller 26 is operative to control the pressure of breathing gas within the conduit 20 and thus within the airway of the patient. Pressure controller 26 is located preferably, although not necessarily, downstream of flow generator 14 and may take the form of an adjustable valve which provides a flow path which is open to the ambient atmosphere via a restricted opening, the valve being adjustable to maintain a constant pressure drop across the opening for all flow rates and thus a constant pressure within conduit 20.

Also interposed in line with conduit 20, preferably downstream of pressure controller 26, is a suitable flow transducer 28 which generates an output signal that is fed as indicated at 29 to a flow signal conditioning circuit 30 for derivation of a signal proportional to the instantaneous flow rate of breathing gas within conduit 20 to the patient.

It will be appreciated that flow generator 14 is not necessarily a positive displacement device. It may be, for example, a blower which creates a pressure head within conduit 20 and provides air flow only to the extent required to maintain that pressure head in the presence of patient breathing cycles, the exhaust opening 24, and action of pressure controller 26 as above described. Accordingly, when the patient is exhaling, peak exhalation flow rates from the lungs may far exceed the flow capacity of exhaust port 24. As a result, exhalation gas backflows within conduit 20 through flow transducer 28 and toward pressure controller 26, and the instantaneous flow rate signal from transducer 28 thus will vary widely within a range from relatively large positive (i.e. toward the patient) flow to relatively large negative (i.e. from the patient) flow.

The instantaneous flow rate signal from flow signal conditioning circuitry 30 is fed as indicated at 32 to a decision module 34, a known comparator circuit for example, and is additionally fed as indicated at 36 to a low pass filter 38. Low pass filter 38 has a cut-off frequency low enough to remove from the instantaneous flow rate input signal most variations in the signal which are due to normal breathing. Low pass filter 38 also has a long enough time constant to ensure that spurious signals, aberrant flow patterns and peak instantaneous flow rate values will not dramatically affect system average flow. That is, the time constant of low pass filter 38 is selected to be long enough that it responds slowly to the instantaneous flow rate signal input. Accordingly, most instantaneous flow rate input signals which could have a large impact on system average flow in the short term have a much smaller impact over a longer term, largely because such instantaneous flow rate signal components will tend to cancel over the longer term. For example, peak instantaneous flow rate values will tend to be alternating relatively large positive and negative flow values corresponding to peak inhalation and exhalation flow achieved by the patient during normal spontaneous breathing. The output of low pass filter 38 thus is a signal which is proportional to the average flow in the system, and this is typically a positive flow which corresponds to average system leakage (including flow from exhaust 24) since, as noted, inhalation and exhalation flow cancel for all practical purposes.

The average flow signal output from the low pass filter 38 is fed as indicated at 40 to decision circuitry 34 where the instantaneous flow rate signal is continually compared to the system average flow signal. The output of the decision circuitry 34 is fed as a drive signal indicated at 42 to control the pressure controller 26. The pressure magnitude of breathing gas within conduit 20 thus is coordinated with the spontaneous breathing effort of the patient 12, as follows.

When the patient begins to inhale, the instantaneous flow rate signal goes to a positive value above the positive average flow signal value. Detection of this increase in decision circuitry 34 is sensed as the start of patient inhalation. The output signal from decision circuitry 34 is fed to pressure controller 26 which, in response, provides higher pressure gas flow within conduit 20 and thus higher pressure within the airway of the patient 12. This is the higher magnitude pressure value of our bi-level CPAP system and is preferred to hereinbelow as IPAP (inhalation positive airway pressure). During inhalation, the flow rate within conduit 20 will increase to a maximum and then decrease as inhalation comes to an end.

At the start of exhalation, air flow into the patient's lungs is nil and as a result the instantaneous flow rate signal will be less than the average flow rate signal which, as noted is a relatively constant positive flow value. The decision circuitry 34 senses this condition as the start of exhalation and provides a drive signal to pressure controller 26 which, in response, provides gas flow within conduit 20 at a lower pressure which is the lower magnitude pressure value of the bi-level CPAP system, referred to hereinbelow as EPAP (exhalation positive airway pressure). As has been noted hereinabove the range of EPAP pressures may include ambient atmospheric pressure. When the patient again begins spontaneous inhalation, the instantaneous flow rate signal again increases over the average flow rate signal, and the decision circuitry once again feeds a drive signal to pressure controller 26 to reinstitute the IPAP pressure.

System operation as above specified requires at least periodic comparison of the input signals 32 and 40 by decision circuitry 34. Where this or other operations are described herein as continual, the scope of meaning to be ascribed includes both continuous (i.e. uninterrupted) and periodic (i.e. at discrete intervals).

As has been noted, the system 10 has a built-in controlled leakage via exhaust port 24 thus assuring that the average flow signal will be at least a small positive flow. During inhalation, the flow sensed by the flow transducer will be the sum of exhaust flow via port 24 and all other system leakage downstream of transducer 28, and inhalation flow within the airway of the patient 12. Accordingly, during inhalation the instantaneous flow rate signal as conditioned by conditioning module 30, will reliably and consistently reflect inhalation flow exceeding the average flow rate signal. During exhalation, the flow within conduit 20 reverses as exhalation flow from the lungs of the patient far exceeds the flow capacity of exhaust port 24. Accordingly, exhalation air backflows within conduit 20 past transducer 28 and toward pressure controller 26. Since pressure controller 26 is operable to maintain set pressure, it will act in response to flow coming from both the patient and the flow generator to open an outlet port sufficiently to accommodate the additional flow volume and thereby maintain the specified set pressure as determined by action of decision circuitry 34.

In both the inhalation and exhalation cycle phases, the pressure of the gas within conduit 20 exerts a pressure within the airway of the patient to maintain an open airway and thereby alleviate airway constriction.

In practice, it may be desirable to provide a slight offset in the switching level within decision circuitry 34 with respect to the average flow rate signal, so that the system does not prematurely switch from the low pressure exhalation mode to the higher pressure inhalation mode. That is, a switching setpoint offset in the positive direction from system average flow may be provided such that the system will not switch to the IPAP mode until the patient actually exerts a significant spontaneous inspiratory effort of a minimum predetermined magnitude. This will ensure that the initiation of inhalation is completely spontaneous and not forced by an artificial increase in airway pressure. A similar switching setpoint offset may be provided when in the IPAP mode to ensure the transition to the lower pressure EPAP mode will occur before the flow rate of air into the lungs of the patient reaches zero (i.e. the switch to EPAP occurs Slightly before the patient ceases inhalation.) This will ensure that the patient will encounter no undue initial resistance to spontaneous exhalation.

From the above description, it will be seen that a novel method of treating sleep apnea is proposed according to which the airway pressure of the patient is maintained at a higher positive pressure during inspiration and a relatively lower pressure during expiration, all without interference with the spontaneous breathing of the patient. The described apparatus is operable to provide such treatment for sleep apnea patients by providing a flow of breathing gas to the patient at positive pressure, and varying the pressure of the aIp flow to provide alternately high and low pressure within the airway of the patient coordinated with the patient's spontaneous inhalation and exhalation.

To provide pressure control, the flow rate of breathing gas to the patient is detected and processed to continually provide a signal which is proportional to the instantaneous breathing gas flow rate in the system. The instantaneous flow rate signal is further processed to eliminate variations attributable to normal patient respiration and other causes thus generating a signal which is proportional to the average or steady state system gas flow. The average flow signal is continually compared with the instantaneous flow signal as a means to detect the state of the patient's spontaneous breathing versus average system flow. When instantaneous flow exceeds the average flow, the patient is inhaling, and in response the pressure of gas flowing to the patient is set at a selected positive pressure, to provide a corresponding positive pressure within the airway of the patient. When comparison of the instantaneous flow rate signal with the average flow signal indicates the patient is exhaling, as for example when the instantaneous flow signal indicates flow equal to or less than the average flow, the pressure of breathing gas to the patient is adjusted to a selected lower pressure to provide a corresponding lower pressure within the airway of the patient.

Figure 2:
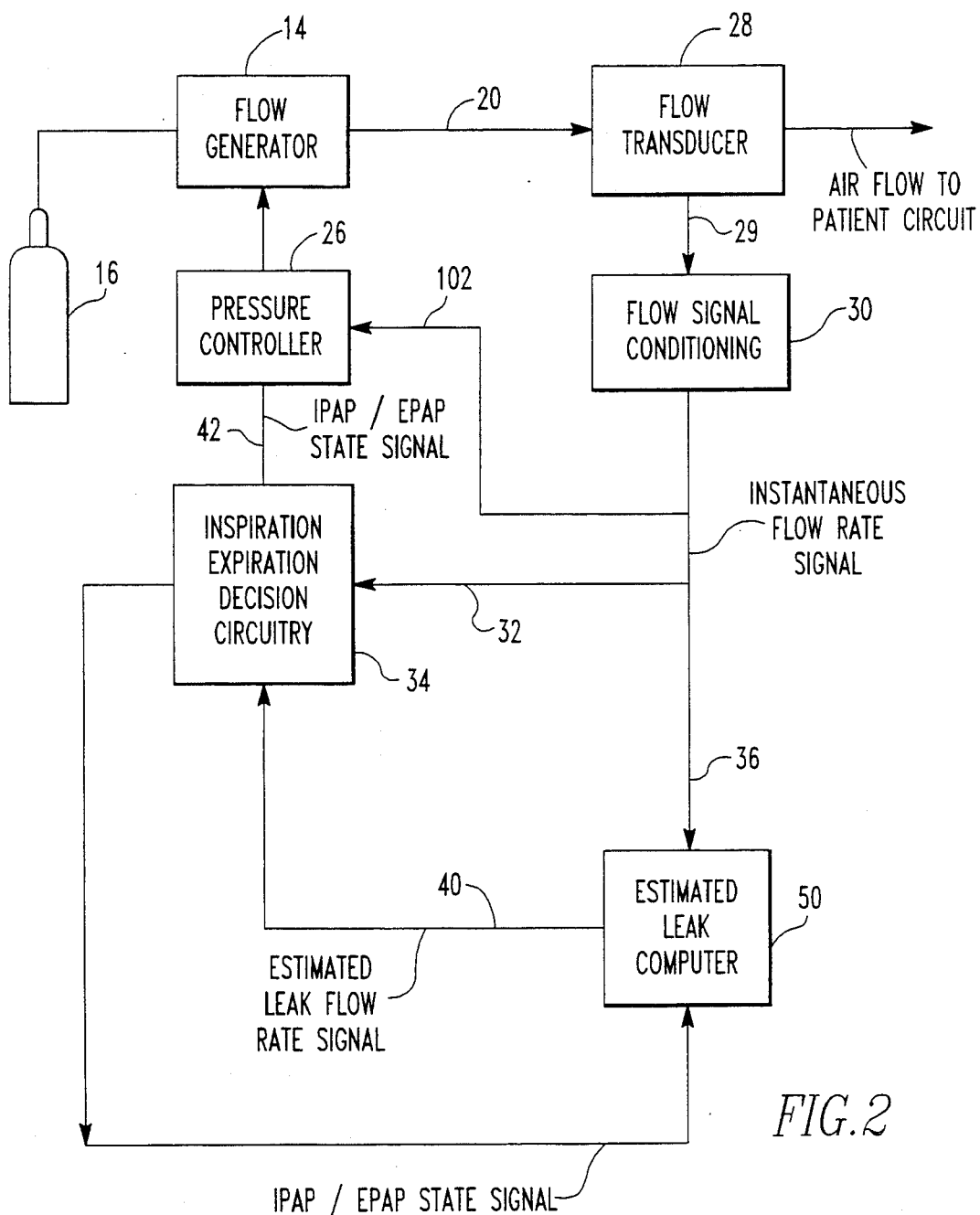
FIG. 2 is a functional block diagram showing an alternative embodiment of the invention.
Figure 3:
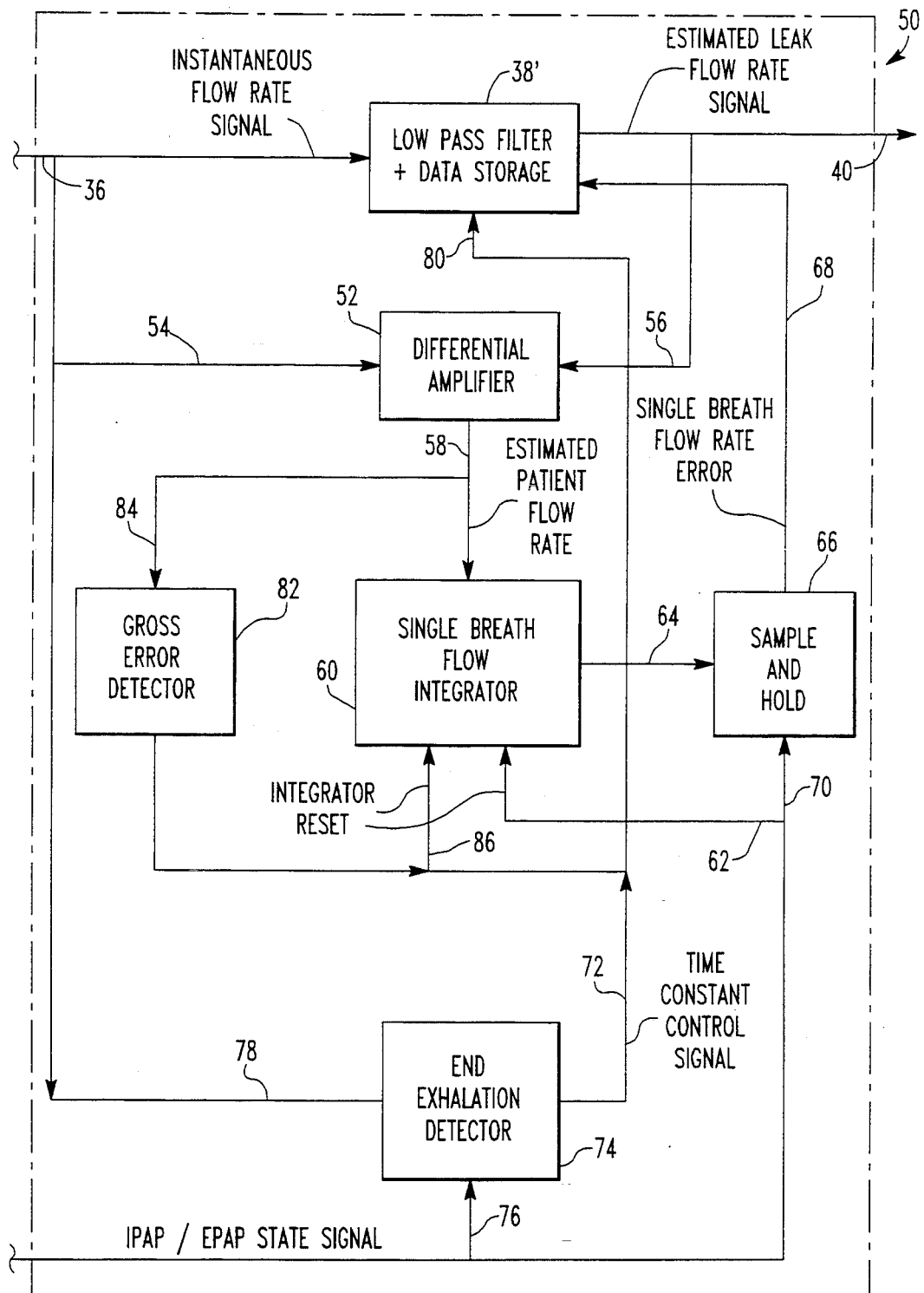
FIG. 3 is a functional block diagram of the Estimated Leak Computer of FIG. 2.

In an alternative embodiment of the invention as shown in FIGS. 2 and 3, the low pass filter 38 is replaced by an estimated leak computer which includes a low pass filter as well as other functional elements as shown in FIG. 3. The remainder of the system as shown in FIG. 2 is similar in most respects to the system shown in FIG. 1. Accordingly, like elements are identified by like numbers, and the description hereinabove of FIG. 1 embodiment also applies generally to FIG. 2.

By using the operative capability of the estimated leak computer 50, as described hereinbelow, it is possible to adjust the reference signal which is fed to decision circuitry 34 on a breath by breath basis rather than merely relying on long term average system flow. To distinguish this new reference signal from average system flow it will be preferred to hereinbelow as the estimated leak flow rate signal on just the estimated leak signal.

As was noted heneinabove, the average system flow rate reference signal changes very slowly due to the long time constant of the low pass filter 38. This operative feature was intentionally incorporated to avoid disturbance of the reference signal by aberrant instantaneous flow rate signal inputs such as erratic breathing patterns. While it was possible to minimize the impact of such aberrations on the average flow rate reference signal, the average flow signal did nevertheless change, although by small increments and only very slowly in response to disturbances, due to the long time constant of the low pass filter, such changes in the reference signal even if transitory could last for a long time.

Additionally, even a small change in the reference signal could produce a very significant effect on system triggering. For example, since the objective is to trigger the system to the IPAP mode when inhalation flow just begins to go positive, small changes in the reference signal could result in relatively large changes in the breathing effort needed to trigger the system to the IPAP mode. In some instances the change in reference signal could be so great that with normal breathing effort the patient would be unable to trigger the system. For example, if the system were turned on before placement of the mask on the face of the patient, the initial free flow of air from the unattached mask could result in a very large magnitude positive value for initial average system flow. If such value were to exceed the maximum inspiratory flow rate achieved in spontaneous respiration by the patient, the system would never trigger between the IPAP and EPAP modes because the decision circuitry would never see an instantaneous flow rate signal greater than the average flow rate signal, at least not until a sufficient number of normal breathing cycles after application of the mask to the patient to bring the reference signal down to a value more closely commensurate with the actual system leak in operation. As has been noted, with the low pass filter this could take a rather long time, during which time the patient would be breathing spontaneously against a uniform positive pressure. This would be tantamount to conventional CPAP and not at all in keeping with the present invention.

In addition to the embodiment based on a reference signal derived from estimated leak flow rate on a breath by breath basis which is controlled totally by spontaneous patient breathing, two further modes of operation also are envisioned, one being spontaneous/timed operation in which the system automatically triggers to the IPAP mode for just long enough to initiate patient inspiration if the system does not sense inspiratory effort within a selected time after exhalation begins. To accomplish this, a timer is provided which is reset at the beginning of each patient inspiration whether the inspiratory cycle was triggered spontaneously or by the timer itself. Thus, only the start of inspiration is initiated by the timer. The rest of the operating cycle in this mode is controlled by spontaneous patient breathing and the circuitry of the system to be described.

A further mode of operation is based purely on timed operation of the system rather than on spontaneous patient breathing effort, but with the timed cycles coordinated to spontaneous patient breathing.

Referring to FIG. 3, the estimated leak computer 50 includes the low pass filter 38' as well as other circuits which are operative to make corrections to the estimated leak flow rate signal based on on-going analysis of each patient breath. A further circuit is provided which is operative to adjust the estimated leak flow rate signal quickly after major changes in system flow such as when the blower has been running prior to the time when the mask is first put on the patient, or after a major leak the system has either started or has been shut off.

The low pass filter 38' also includes a data storage capability whose function will be described hereinbelow.

The low pass filter 38' operates substantially as described above with reference to FIG. 1 in that it provides a long term average of system flow which is commensurate with steady state system leakage including the flow capacity of the exhaust port 24. This long term average is operative in the FIG. 3 embodiment to adjust the estimated leak flow rate reference signal only when system flow conditions are changing very slowly.

To provide breath by breath analysis and adjustment of the reference signal, a differential amplifier 52 receives the instantaneous flow rate signal as indicated at 54, and the estimated leak signal output from low pass filter 38' as indicated at 56.

The output of differential amplifier 52 is the difference between instantaneous flow rate and estimated leak flow rate, or in other words estimated instantaneous patient flow rate. This will be clear upon considering that instantaneous flow is the sum of patient flow plus actual system leakage. The estimated patient flow signal output from differential amplifier 52 is provided as indicated at 58 to a flow integrator 60 which integrates estimated patient flow breath by breath beginning and ending with the trigger to IPAP. Accordingly, an additional input to the flow integrator 60 is the IPAP/EPAP state signal as indicated at 62. The IPAP/EPAP state signal is the same as the drive signal provided to pressure controller 26; that is, it is a signal indicative of the pressure state, as between IPAP and EPAP, of the system. The state signal thus may be used to mark the beginning and end of each breath for purposes of breath by breath integration by integrator 60.

If the estimated leak flow rate signal from low pass filter 38' is equal to the true system leak flow rate, and if the patient's inhaled and exhaled volumes are identical for a given breath (i.e. total positive patient flow equals total negative patient flow for a given breath), then the integral calculated by integrator 60 will be zero and no adjustment of estimated leak flow rate will result. When the integral calculated by integrator 60 is non-zero, the integral value in the form of an output signal from integrator 60 is provided as indicated at 64 to a sample and hold module 66. Of course, even with a zero value integral, an output signal may be provided to module 66, but the ultimate result will be no adjustment of the estimated leak flow rate signal.

A non-zero integral value provided to module 66 is further provided to module 38' as indicated at 68 with each patient breath by operative action of the IPAP/EPAP state signal upon module 66 as indicated at 70. The effect of a non-zero integral value provided to module 38' is an adjustment of the estimated leak flow rate signal proportional to the integral value and in the direction which would reduce the integral value towards zero on the next breath if all other conditions remain the same.

With this system, if the patient's net breathing cycle volume is zero, and if the system leak flow rate changes, the integrator circuit will compensate for the change in leak flow rate by incremental adjustments to the estimated leak flow rate within about ten patient breaths.

The integrator circuit 60 also will adjust the estimated leak flow rate signal in response to non-zero net volume in a patient breathing cycle. It is not unusual for a patient's breathing volume to be non-zero. For example, a patient may inhale slightly more on each breath than he exhales over several breathing cycles, and then follow with a deeper or fuller exhalation. In this case, the integrator circuit would adjust the estimated leak flow rate signal as if the actual system leak rate had changed; however, since the reference signal correction is only about one tenth as large as would be required to make the total correction in one breath, the reference signal will not change appreciably over just one or two breaths. Thus, the integrator circuit accommodates both changes in system leakage and normal variations in patient breathing patterns. The integrator circuit normally would be active, for example, during rapid patient breathing.

An end exhalation module 74 is operative to calculate another data component for use in estimating the system leak flow rate as follows. The module 74 monitors the slope of the instantaneous flow rate wave form. When the slope value is near zero during exhalation (as indicated by the state signal input 76) the indication is that the flow rate is not changing. If the slope of the instantaneous flow rate signal wave form remains small after more than one second into the respiratory phase, the indication is that exhalation has ended and that the net flow rate at this point thus is the leak flow rate. However, if estimated patient flow rate is non-zero at the same time, one component of the instantaneous flow rate signal must be patient flow.

When these conditions are met, the circuit adjusts the estimated leak flow rate slowly in a direction to move estimated patient flow rate toward zero to conform to instantaneous patient flow conditions expected at the end of exhalation. The adjustment to estimated leak flow rate is provided as an output from module 74 to low pass filter 38' as indicated at 80. When this control mechanism takes effect, it disables the breath by breath volume correction capability of integrator circuit 60 for that breath only.

The output of module 74 is a time constant control signal which is provided to low pass filter 38' to temporarily shorten the time constant thereof for a sufficient period to allow the estimated leak flow rate to approach the instantaneous flow rate signal at that specific instant. It will be noted that shortening the low pass filter time constant increases the rapidity with which the low pass filter output (a system average) can adjust toward the instantaneous flow rate signal input.

Another component of estimated leak flow rate control is a gross error detector 82 which acts when the estimated patient flow rate, provided thereto as indicated at 84, is away from zero for more than about 5 seconds. Such a condition may normally occur, for example, when the flow generator 14 is running before mask 22 is applied to the patient. This part of the control system is operative to stabilize operation quickly after major changes in the leak rate occur.

In accordance with the above description, it will be seen that low pass filter 38' acts on the instantaneous flow rate signal to provide an output corresponding to average system flow, which is system leakage since patient inspiration and expiration over time constitutes a net positive flow of zero. With other enhancements, as described, the system average flow can be viewed as an estimate of leakage flow rate.

The differential amplifier 52 processes the instantaneous flow rate signal and the estimated leak flow rate signal to provide an estimated patient flow rate signal which is integrated and non-zero values of the integral are fed back to module 38' to adjust the estimated leak flow rate signal on a breath by breath basis. The integrator 60 is reset by the IPAP/EPAP state signal via connection 62.

Two circuits are provided which can override the integrator circuit, including end exhalation detector 74 which provides an output to adjust the time constant of low pass filter 38' and which also is provided as indicated at 86 to reset integrator 60. Gross error detector 82 is also provided to process estimated patient flow rate and to provide an adjustment to estimated leak flow rate under conditions as specified. The output of module 82 also is utilized as an integrator reset signal as indicated at 86. It will be noted that the integrator 60 is reset with each breath of the patient if, during that breath, it is ultimately overridden by module 74 or 82. Accordingly, the multiple reset capabilities for integrator 60 as described are required.

In operation, the system may be utilized in a spontaneous triggering mode, a spontaneous/timed mode or a purely timed mode of operation. In spontaneous operation, decision circuitry 34 continuously compares the instantaneous flow rate with estimated leak flow rate. If the system is in the EPAP state or mode, it remains there until instantaneous flow rate exceeds estimated leak flow rate by approximately 40 cc per second. When this transition occurs, decision circuitry 34 triggers the system into the IPAP mode for 150 milliseconds. The system will then normally remain in the IPAP mode as the instantaneous flow rate to the patient will continue to increase during inhalation due to spontaneous patient effort and the assistance of the increased IPAP pressure.

After the transition to the IPAP mode in each breath, a temporary offset is added to the estimated leak flow rate reference signal. The offset is proportional to the integral of estimated patient flow rate beginning at initiation of the inspiratory breath so that it gradually increases with time during inspiration at a rate proportional to the patient's inspiratory flow rate. Accordingly, the flow rate level above estimated leak flow needed to keep the system in the IPAP mode during inhalation decreases with time from the beginning of inhalation and in proportion to the inspiratory flow rate. With this enhancement, the longer an inhalation cycle continues, the larger is the reference signal below which instantaneous flow would have to decrease in order to trigger the EPAP mode. For example, if a patient inhales at a constant 500 cc per second until near the end of inspiration, a transition to EPAP will occur when his flow rate drops to about 167 cc per second after one second, or 333 cc per second after two seconds, or 500 cc per second after three seconds, and so forth. For a patient inhaling at a constant 250 cc per second, the triggers would occur at 83, 167 and 250 cc per second at one, two and three seconds into IPAP, respectively.

In this way, the EPAP trigger threshold comes up to meet the inspiratory flow rate with the following benefits. First, it becomes easier and easier to end the inspiration cycle with increasing time into the cycle. Second, if a leak develops which causes an increase in instantaneous flow sufficient to trigger the system into the IPAP mode, this system will automatically trigger back to the EPAP mode after about 3.0 seconds regardless of patient breathing effort. This would allow the volume-based leak correction circuit (i.e. integrator 60) to act as it is activated with each transition to the IPAP mode, Thus, if a leak develops suddenly, there will be a tendency toward automatic triggering rather than spontaneous operation for a few breaths, but the circuit will not be locked into the IPAP mode.

Upon switching back to the EPAP mode, the trigger threshold will remain above the estimated leak flow rate for approximately 500 milliseconds to allow the system to remain stable in the EPAP mode without switching again while the respective flow rates are changing. After 500 milliseconds, the trigger threshold offset is reset to zero to await the next inspiratory effort.

The normal state for the circuit is for it to remain in the EPAP mode until an inspiratory effort is made by the patient. The automatic corrections and adjustments to the reference signal are effective to keep the system from locking up in the IPAP mode and to prevent auto-triggering while at the same time providing a high level of sensitivity to inspiratory effort and rapid adjustment for changing leak conditions and breathing patterns.

In the spontaneous/timed mode of operation, the system performs exactly as above described with reference to spontaneous operation, except that it allows selection of a minimum breathing rate to be superimposed upon the spontaneous operating mode. If the patient does not make an inspiratory effort within a predetermined time, the system will automatically trigger to the IPAP mode for 200 milliseconds. The increased airway pressure for this 200 milliseconds will initiate patent inspiration and provide sufficient time that spontaneous patient flow will exceed the reference signal so that the rest of the cycle may continue in the spontaneous mode as above described. The breaths per minute timer is reset by each trigger to IPAP whether the transition was triggered by the patient or by the timer itself.

In the timed operating mode, all triggering between IPAP and EPAP modes is controlled by a timer with a breath per minute control being used to select a desired breathing rate from, for example, 3 to 30 breaths per minute. If feasible, the selected breathing rate is coordinated to the patient's spontaneous breathing rate. The percent IPAP control is used to set the fraction of each breathing cycle to be spent in the IPAP mode. For example, if the breaths per minute control is set to 10 breaths per minute (6 seconds per breath) and the percent IPAP control is set to 33%, then the flow generator will spend, in each breathing cycle, two seconds in IPAP and four seconds in EPAP.

Figure 4:
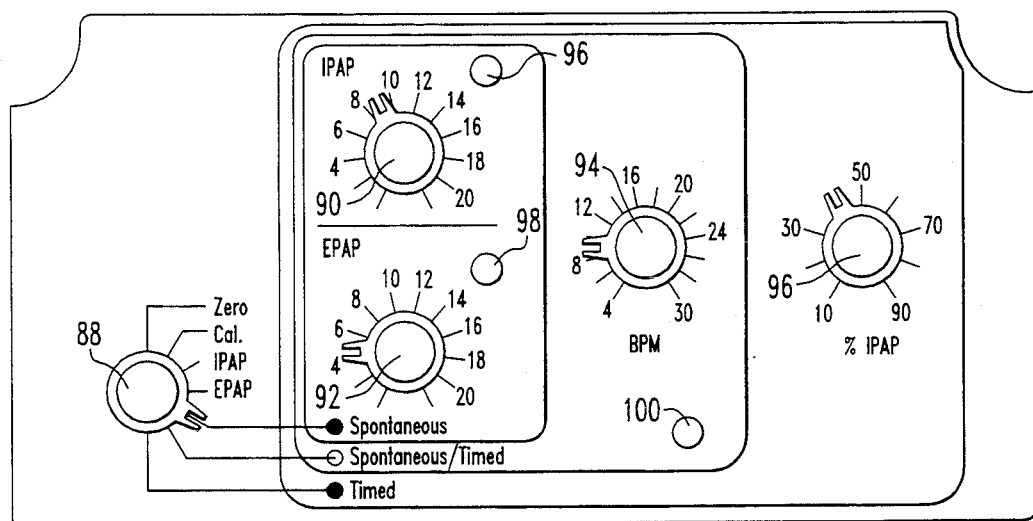
FIG. 4 is a frontal elevation of a control panel for the apparatus of this invention.

FIG. 4 illustrates a control panel for controlling the system above described and including a function selector switch which includes function settings for the three operating modes of spontaneous, spontaneous/timed, and timed as above described. The controls for spontaneous mode operation include IPAP and EPAP pressure adjustment controls 90 and 92, respectively. These are used for setting the respective IPAP and EPAP pressure levels. In the spontaneous/timed mode of operation, controls 90 and 92 are utilized as before to set IPAP and EPAP pressure levels, and breaths per minute control 94 additionally is used to set the minimum desired breathing rate in breaths per minute. In the timed mode of operation, controls 90, 92 and 94 are effective, and in addition the per cent IPAP control 96 is used to set the time percentage of each breath to be spent in the IPAP mode.

Lighted indicators such as LED's 96, 98 and 100 are also provided to indicate whether the system is in the IPAP or EPAP state, and to indicate whether in the spontaneous/timed mode of operation the instantaneous state of the system is spontaneous operation or timed operation.

Figure 5:
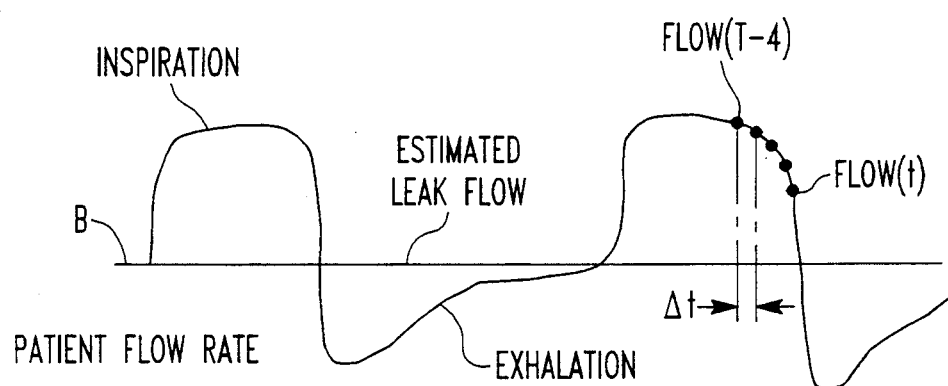
FIG. 5 shows a trace of patient flow rate versus time pertaining to an alternative embodiment of the invention.

An alternative embodiment of the invention contemplates detecting the beginning of inspiration and expiration by reference to a patient flow rate wave form such as shown in FIG. 5. Comparison of instantaneous flow rate with average flow rate as set forth hereinabove provides a satisfactory method for determining whether a patient is inhaling or exhaling; however, other means for evaluating instantaneous flow rate can also be used, and these may be used alone or in combination with average flow rate.

For example, FIG. 5 shows a typical patient flow rate wave form with inspiration or inhalation flow shown as positive flow above base line B and exhalation flow shown as negative flow below base line B. The flow rate wave form may thus be sampled at discrete time intervals. The current sample is compared with that taken at an earlier time. This approach appears to offer the benefit of higher sensitivity to patient breathing effort in that it exhibits less sensitivity to errors in the estimated system leakage, as discussed hereinabove.

Normally, the estimated inspiratory and expiratory flow rate wave forms will change slowly during the period beginning after a few hundred miliseconds into the respective inspiratory and expiratory phases, up until the respective phase is about to end. Samples of the flow rate wave form are taken periodically, and the current sample is compared repeatedly with a previous sample. During inspiration, if the magnitude of the current sample is less than some appropriate fraction of the comparison sample, then the inspiration phase is deemed to be finished. This condition thus can be used to trigger a change to the desired exhalation phase pressure. The same process can be used during exhalation to provide a trigger condition for the changeover to inhalation pressure.

Figure 6:
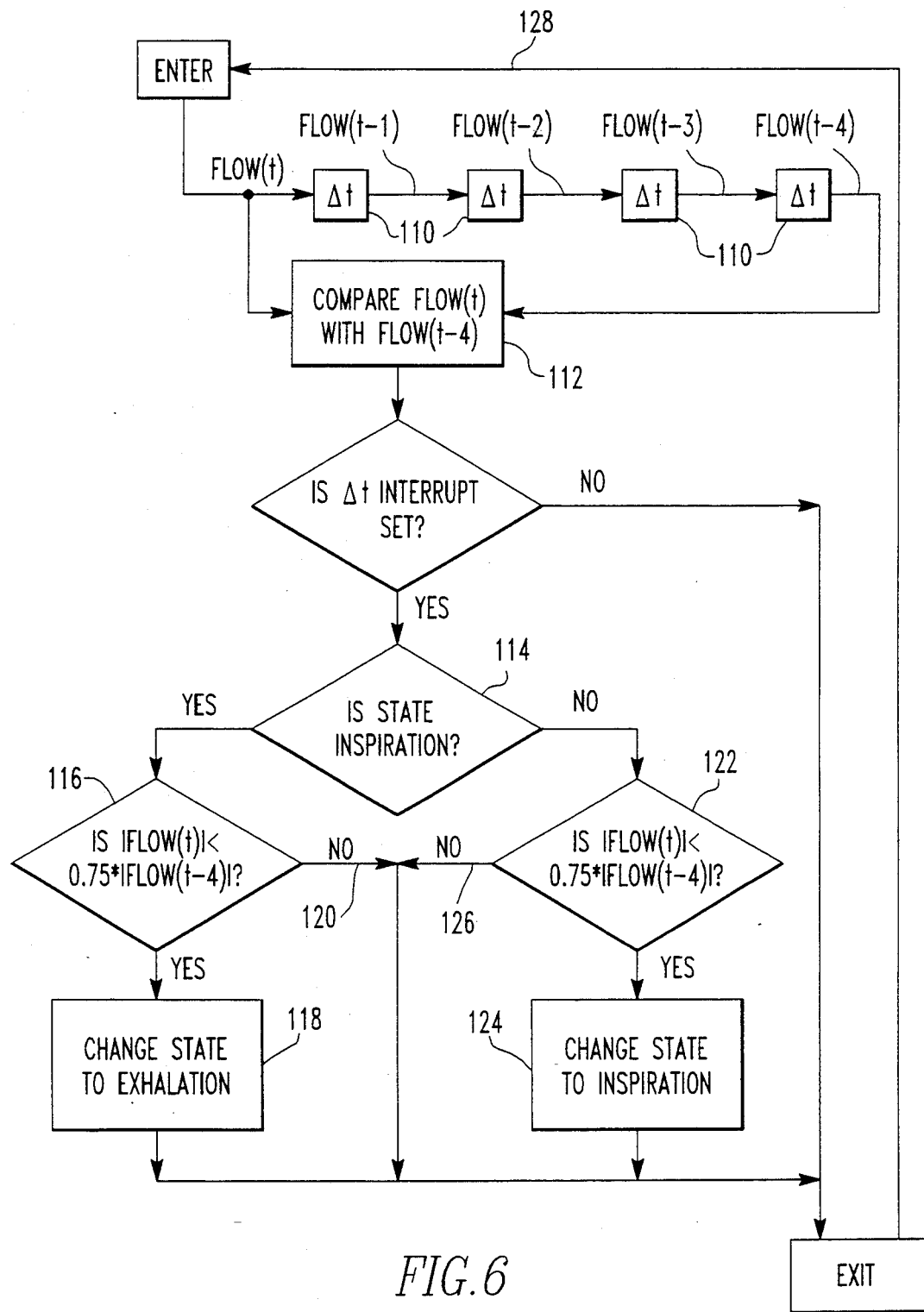
FIG. 6 is a flow diagram relating to the same alternative embodiment of the invention.

FIG. 6 illustrates a flow diagram for a suitable algorithm showing repeated sampling of the patient flow rate wave form at time intervals $\Delta t$, as shown at 110, and repeated comparison of the flow at current time t with a prior sampling, for example the flow at time t-4 as indicated at 112. Of course, the time increment between successive samplings is small enough that the comparison with the value observed in the fourth prior sampling event covers a suitably small portion of the flow rate wave form. For example, as shown in FIG. 5 the designations for flow sampled at time t, the sample value taken for sampling events prior at time t-4, and the time interval $\Delta t$ illustrate one suitable proportionate relationship between $\Delta t$ and the time duration of a patient breath. This is, however, only an illustration. In fact, electronic technology such as disclosed hereinabove would be capable of performing this algorithm using much smaller $\Delta t$ intervals, provided other parameters of the algorithm, such as the identity of the comparison sample and/or the proportion relationship between the compared samples, are adjusted accordingly.

Continuing through the flow chart of FIG. 6, if the patient's state of breathing is inspiration (114), the current flow sample value is compared with the sample value observed t-4 sampling events prior. If the current flow sample value is less than 75% of the comparison flow value (116), the system triggers a change in state to the exhalation phase (118). If the current flow sample value is not less than 75% of the comparison value (120), no change in breathing state is triggered.

If the breathing state is not inspiration, and the current flow sample value is less than 75% of the selected comparison value (122), then an expiration phase, rather than an inspiration phase, is completed and the system is triggered to change the state of breathing to inspiration (124). If the specified flow condition is not met, again no change in breathing phase is triggered (126).

The routine characterized by FIG. 6 repeats continuously as indicated at 128, each time comparing a current flow sample with the fourth (or other suitable) prior sample to determine whether the system should trigger from one breathing phase to the other.

Of course, it will be understood that the embodiment set forth above with reference to FIGS. 5 and 6 does not trigger changes in breathing per se within the context of the invention as set forth in the balance of the specification. Rather, in that context the FIGS. 5 and 6 embodiment merely detects changes between inspiration and expiration in spontaneous patient breathing, and triggers the system to supply the specified higher or lower airway pressure as set forth hereinabove.

According to the above description there is provided by the instant invention a novel and improved method and apparatus for the treatment of sleep apnea. Of course, we have contemplated various alternative and modified embodiments of the invention of which the above described are exemplary as the presently contemplated best modes for carrying out the invention. Such alternative embodiments would also surely occur to others skilled in the art, once apprised of the invention. For example, it may be desirable to provide a flow compensation signal to pressure controller 26 as indicated at 102 in FIG. 2 to compensate for flow resistance inherent in the circuit; a non-rebreathing valve may be utilized in lieu of exhaust port 24 at mask 22; and the like. Accordingly, it is intended that the invention be construed broadly and limited only by the scope of the claims appended hereto.

We claim:

1. A method of providing a flow of gas within a predetermined flow path which includes a patient's respiratory system for breathing by such a patient in repeated breathing cycles each including an inspiratory phase during which said flow of gas includes gas flowing to such a patient's lungs and an expiratory phase during which said flow of gas includes gas flowing from such a patient's lungs, said method comprising the steps of:
   providing said flow of gas at a positive pressure at least equal to ambient atmospheric pressure to maintain the patient's airway at such a positive pressure during said repeated breathing cycles;
   monitoring said flow of gas;
   from said monitoring, determining at least one of an instantaneous flow rate and an average flow rate of such gas;
   utilizing said at least one of said instantaneous flow rate and said average flow rate to identify the occurrence of said inspiratory and expiratory phases; and
   coordinating the patient's airway pressure with said occurrence of each said inspiratory and expiratory phases in a manner that said positive pressure is maintained in the patient's airway during a sequence of said inspiratory and expiratory phases with the magnitude of said positive pressure during selected ones of said expiratory phases in said sequence being less than the magnitude of said positive pressure during the respective immediately preceding inspiratory phases.

2. The method as set forth in claim 1 wherein said determining step includes determining at least one of said instantaneous and average flow rates of such gas flowing between such a source and the airway of such a patient.

3. The method as set forth in claim 1 wherein said supplying step includes the supplying of breathing gas under pressure via a breathing appliance interfacing with such a patient.

4. The method as set forth in claim 1 wherein said positive pressure is maintained in the patient's airway substantially continuously during said sequence of said inspiratory and expiratory phases.

5. The method as set forth in claim 1 wherein said monitoring of said flow of gas is continual monitoring thereof.

6. The method as set forth in claim 1 wherein said determining at least one of an instantaneous flow rate and an average flow rate is continual determining thereof, 7. The method as set forth in claim 1 wherein said determining step includes determining both of said instantaneous flow rate and said average flow rate, and said utilizing step includes utilizing both of said instantaneous flow rate and said average flow rate.

8. The method as set forth in claim 1 wherein at least one of said magnitudes of said positive pressure is a substantially constant magnitude of positive pressure.

9. A method of medical treatment for a patient comprising the steps of:
   providing a flow of breathing gas from a source for delivery to the airway of such a patient at selected higher and lower pressure magnitudes at least as great as ambient atmospheric pressure and permitting said flow of gas to pass from the patient;
   monitoring said flow to detect an instantaneous flow rate of such breathing gas;
   processing selected parameters including said instantaneous flow rate to provide a reference indicia corresponding to an average flow rate of such breathing gas; and
   utilizing at least one of said instantaneous flow rate and said reference indicia to select one of said higher and said lower pressure magnitudes to be applied in the airway of such a patient.

10. The method as set forth in claim 9 wherein said monitoring step includes monitoring said flow of gas to detect an instantaneous flow rate of such breathing gas flowing between said source and the airway of such a patient.

11. The method as set forth in claim 9 including the additional step of continually repeating said selecting step.

12. The method as set forth in claim 9 wherein said flow of breathing gas is a substantially continuous flow of breathing gas.

13. The method as set forth in claim 9 wherein said selecting step includes selecting said higher pressure magnitude when said instantaneous flow rate is greater than said reference indicia, and selecting said lower pressure magnitude when said instantaneous flow rate is less than said reference indicia.

14. The method as set forth in claim 9 wherein said processing step includes adjusting a previously determined value of said reference indicia to provide an adjusted value thereof.

15. The method as set forth in claim 14 wherein said previously determined value of said reference indicia is included among said selected parameters.

16. The method as set forth in claim 15 wherein said processing step includes first processing of said instantaneous flow rate to provide a time average of the flow rate of breathing gas resulting from said providing step as a first component of said reference indicia.

17. The method as set forth in claim 16 wherein said processing step additionally includes second processing of said instantaneous flow rate and said reference indicia to provide a measure of the net flow of breathing gas to such a patient for each spontaneous patient breath as a second component of said reference indicia.

18. The method as set forth in claim 17 wherein said processing step additionally includes third processing of said instantaneous flow rate and the occurrence of said selecting step to provide a measure of said instantaneous flow rate at the end of selected patient expiratory cycles as a third component of said reference indicia.

19. The method as set forth in claim 18 wherein said first, second and third processing steps are carried out simultaneously.

20. The method as set forth in claim 19 wherein said simultaneous first, second and third processing steps are carried out repetitively.

21. The method as set forth in claim 20 wherein said third processing step overrides said second processing step when said measure of said instantaneous flow rate at the end of said selected patient expiratory cycles differs from said reference indicia.

22. The method as set forth in claim 9 wherein said providing step includes providing said flow of breathing gas via a breathing gas delivery appliance worn by such a patient.

23. The method as set forth in claim 9 wherein said monitoring of said flow of gas includes continual monitoring thereof.

24. The method as set forth in claim 9 wherein said processing selected parameters includes continual processing thereof.

25. The method as set forth in claim 9 wherein said utilizing at least one of said instantaneous flow rate and said reference indicia includes utilizing both of said instantaneous flow rate and said reference indicia.

26. The method as set forth in claim 9 wherein at least one of said higher and lower pressure magnitudes is a substantially constant pressure magnitude.

27. An apparatus for delivering pressurized gas to the airway of a patient who is breathing in repeated breathing cycles each including an inspiratory phase and an expiratory phase comprising:
   a gas flow generator means for providing a flow of gas;
   supply means for delivery of said flow of gas from said flow generator means to the airway of such a patient;
   exhaust means for allowing said flow of gas to pass from the airway of such a patient;
   pressure controller means cooperable with said flow generator means to provide said flow of gas within said supply means for delivery to the airway of such a patient at selectively variable pressures;
   monitoring means for monitoring the flow-rate of said flow of gas;
   processor means which is cooperable with said monitoring means to provide a first indicia corresponding to an instantaneous flow rate of said flow of gas;
   said processor means being further cooperable with said monitoring means to provide a reference indicia corresponding to an approximate average flow rate of said flow of gas;
   decision means operable to utilize at least one of said first indicia and said reference indicia to identify the occurrence of said inspiratory and expiratory phases; and
   said decision means being cooperable with said pressure controller means to control the pressure of such gas within said supply means for varying the pressure applied within the airway of such a patient in response to identification of the occurrence of said inspiratory and expiratory phases.

28. The apparatus as set forth in claim 27 wherein said first indicia corresponds to an instantaneous flow rate of such gas in said supply means and said reference indicia corresponds to an approximate average flow rate of such gas in said supply means.

29. The apparatus as set forth in claim 27 wherein said decision means is operable to utilize both of said first indicia and said reference indicia, and is further operable to adjust said pressure controller means to provide a higher pressure within the airway of such a patient when said first indicia exceeds said reference indicia, and to provide a lower pressure within the airway of such a patient when said first indicia is less than said reference indicia.

30. The apparatus as set forth in claim 29 wherein said processor means includes processing elements operable to adjust an existing value of said reference indicia to provide an adjusted value thereof.

31. The apparatus as set forth in claim 30 wherein said processing elements include means for processing said first indicia to provide a time average of the flow rate of such gas within said supply means as a first component of said reference indicia.

32. The apparatus as set forth in claim 31 wherein said processing elements further include means for processing said first indicia and said reference indicia to provide a measure of the gas flow within said supply means during a predeterminable time period as a second component of said reference indicia.

33. The apparatus as set forth in claim 32 wherein said predeterminable time period is a single complete breathing cycle of such a patient including one inspiratory cycle and one expiratory cycle in sequence.

34. The apparatus as set forth in claim 33 wherein said processing elements further include means for processing said first indicia to provide a measure of the value of said first indicia at the end of any such complete breathing cycle by such a patient as a third component of said reference indicia.

35. The apparatus as set forth in claim 27 wherein said monitoring means is operable for continually monitoring the flow rate of said flow of gas.

36. The apparatus as set forth in claim 27 wherein said processor means includes first and second processor means, respectively, with one of said first and second processor means being cooperable with said monitoring means to provide said first indicia and the other of said first and second processor means being cooperable with said one of said processor means to provide said reference indicia.

37. The apparatus as set forth in claim 27 wherein said decision means is operable to utilize both of said first indicia and said reference indicia to identify the occurrence of said inspiratory and expiratory phases.

38. A method of treating sleep apnea syndrome comprising the steps of:
   providing a flow of breathing gas from a source for breathing by a patient;
   supplying said flow of breathing gas to the airway of such a patient during inspiration;
   permitting said flow of breathing gas to pass from such a patient during expiration;
   monitoring said flow of breathing gas to detect flow conditions of said flow of breathing gas;
   from said monitoring, determining at least one of an instantaneous flow rate and an average flow rate of said flow of breathing gas;
   utilizing said at least one of said instantaneous flow rate and said average flow rate to identify the occurrence of each inspiratory and expiratory phase of the patient's respiration cycle; and
   coordinating the patient's airway pressure with said occurrence of each said inspiratory and expiratory phase to maintain positive pressure in the patient's airway during a sequence of said inspiratory and said expiratory phases with the magnitude of said positive pressure maintained during selected ones of said expiratory phases in said sequence being less than the magnitude of said positive pressure maintained during the respective immediately preceding inspiratory phases.

39. The method as set forth in claim 38 wherein said determining step includes determining said at least one of an instantaneous flow rate and an average flow rate of said flow of breathing gas.

40. The method as set forth in claim 38 wherein said determining step includes continually determining at least one of an instantaneous flow rate and an average flow rate of such breathing gas.

41. The method as set forth in claim 38 wherein said determining at least one of an instantaneous flow rate and an average flow rate includes determining both of said instantaneous flow rate and said average flow rate, and said utilizing at least one of said instantaneous flow rate and said average flow rate includes utilizing both of said instantaneous flow rate and said average flow rate.

42. The method as set forth in claim 38 wherein the magnitude of said positive pressure maintained during at least one of said expiratory and said inspiratory phases is a constant magnitude of positive pressure.

43. The method as set forth in claim 38 wherein said positive pressure is maintained substantially continuously in the patient's airway.

44. A method of treating sleep apnea syndrome comprising the steps of:
providing a flow of breathing gas from a source for delivery to the airway of a patient at selected higher and lower pressure magnitudes at least as great as ambient atmospheric pressure;
permitting said flow of breathing gas to pass from such a patient;
monitoring said flow of breathing gas to detect an instantaneous flow rate of said breathing gas;
processing selected parameters including said instantaneous flow rate to provide a reference indicia corresponding to an average flow rate of said breathing gas; and
utilizing at least one of said instantaneous flow rate and said reference indicia to select one of said higher and said lower pressure magnitudes for said supply flow of breathing gas.

45. The method as set forth in claim 44 wherein said instantaneous flow rate and average flow rate of said breathing gas are, respectively, instantaneous and average flow rates of said flow of breathing gas.

46. The method as set forth in claim 44 wherein said monitoring of said flow of breathing gas includes continual monitoring thereof.

47. The method as set forth in claim 44 wherein said processing selected parameters includes continual processing thereof.

48. The method as set forth in claim 44 wherein said utilizing at least one of said instantaneous flow rate and said reference indicia includes utilizing both of said instantaneous flow rate and said reference indicia.

49. A method of treating obstructive sleep apnea comprising the steps of:
preventing episodes of airway obstruction by applying positive pressure greater than ambient atmospheric pressure within the airway of a patient;
applying said positive pressure by supplying gas at a positive pressure to the airway of such a patient;
adjusting the pressure of said gas in the patient's airway to coordinate the patient's airway pressure with the occurrence of alternating inspiratory and expiratory phases of the patient's respiration in a manner to maintain said positive pressure in the patient's airway during a sequence of said inspiratory and expiratory phases with the magnitude of said positive pressure during each said expiratory phase being less than the magnitude of said positive pressure during the immediately preceding inspiratory phase, respectively; and
maintaining the magnitude of said positive pressure within the patient's airway at a value sufficient to prevent said episodes of airway obstruction during said sequence of inspiratory and expiratory phases.

50. The method as set forth in claim 49 wherein said applying said positive pressure step includes substantially continuously applying said positive pressure.

51. The method as set forth in claim 49 wherein said adjusting the pressure of said gas in the patient's airway to coordinate the patient's airway pressure with the occurrence of alternating inspiratory and expiratory phases of the patient's respiration in a manner to maintain said positive pressure includes substantially continuously maintaining said positive pressure.

52. The method as set forth in claim 49 wherein the magnitude of positive pressure applied during at least said inspiratory phases or said expiratory phases is a substantially constant magnitude of positive pressure.

53. A method of treating sleep apnea syndrome comprising the steps of:
providing a flow of breathing gas from a source for delivery to the airway of a patient at selected higher and lower pressure magnitudes at least as great as ambient atmospheric pressure;
permitting said flow of breathing gas to pass from such a patient;
monitoring said flow of breathing gas to detect an instantaneous flow rate of said breathing gas;
processing selected parameters including said instantaneous flow rate to provide a reference indicia; and
utilizing at least one of said instantaneous flow rate and said reference indicia to select one of said higher and said lower pressure magnitudes for said supply flow of breathing gas.

54. The method as set forth in claim 53 wherein said monitoring of said flow of breathing gas includes continual monitoring thereof.

55. The method as set forth in claim 53 wherein said processing selected parameters includes continual processing thereof.

56. The method as set forth in claim 53 wherein said utilizing at least one of said instantaneous flow rate and said reference indicia includes utilizing both of said instantaneous flow rate and said reference indicia.

57. A method of treating obstructive sleep apnea comprising the steps of:
preventing episodes of airway obstruction by applying positive pressure greater than ambient atmospheric pressure within the airway of a patient;
applying said positive pressure by supplying gas at a positive pressure to the airway of such a patient throughout a sequence of alternating inspiratory and expiratory phases of the patient's respiration; and adjusting said positive pressure in the patient's airway to coordinate the patient's airway pressure with the occurrence of said alternating inspiratory and expiratory phase in a manner that the magnitude of said positive pressure applied during at least some of said inspiratory phases is greater than the magnitude of said positive pressure applied during the expiratory phases immediately following said at least some of said inspiratory phases, respectively; and maintaining the magnitude of said positive pressure within the patient's airway at a value sufficient to prevent said episodes of airway obstruction during said sequence of alternative inspiratory and expiratory phases.

58. The method as set forth in claim 57 wherein said applying said positive pressure includes substantially continuously applying.

59. The method as set forth in claim 57 wherein said positive pressure applied during at least said inspiratory phases or said expiratory phases is a substantially constant positive pressure.

60. The method as set forth in claim 57 wherein said sequence consists of a single inspiratory phase followed by a single expiratory phase of the patient's respiration.

61. A method of treating obstructive sleep apnea comprising the steps of:

preventing episodes of airway obstruction by applying positive pressure greater than ambient atmospheric pressure within the airway of a patient;

applying said positive pressure by supplying gas at said positive pressure to the airway of such a patient throughout a sequence of alternating inspiratory and expiratory phases of the patient's respiration;

adjusting said positive pressure in the airway of a patient such that the magnitude of said positive pressure applied during at least some of said inspiratory phases is greater than the magnitude of said positive pressure applied during the expiratory phases immediately following said at least some of said inspiratory phases, respectively; and maintaining the magnitude of said positive pressure within the patient's airway at a value sufficient to prevent said episodes of airway obstruction during said sequence of inspiratory and expiratory phases.

62. The method as set forth in claim 61 wherein said sequence consists of a single inspiratory phase followed by a single expiratory phase of the patient's respiration.

63. A method of treating obstructive sleep apnea comprising the steps of:

preventing episodes of airway obstruction by applying positive pressure greater than ambient atmospheric pressure within the airway of a patient;

applying said positive pressure by supplying gas at said positive pressure to the airway of such a patient;

adjusting said positive pressure in the patient's airway throughout a sequence of patient respiration phases comprised of at least one inspiratory phase and at least one expiratory phase in a manner that the magnitude of said positive pressure in the patient's airway during said inspiratory phases is greater than the magnitude of said positive pressure in the patient's airway during said expiratory phases immediately following the respective said inspiratory phases; and maintaining the magnitude of said positive pressure within the patient's airway at a value sufficient to prevent said episodes of airway obstruction during said sequence of inspiratory and expiratory phases.

64. A method of treating incidents of airway obstruction which occur during sleep comprising the steps of:

preventing episodes of airway obstruction by applying positive pressure greater than ambient atmospheric pressure within the airway of a patient;

applying said positive pressure by supplying gas at a positive pressure to the airway of such a patient;

adjusting the pressure of said gas in the patient's airway to coordinate the patient's airway pressure with the occurrence of alternating inspiratory and expiratory phases of the patient's respiration in a manner to maintain said positive pressure in the patient's airway during a sequence of said inspiratory and expiratory phases with the magnitude of said positive pressure during each said expiratory phase being less than the magnitude of said positive pressure during the immediately preceding inspiratory phase, respectively; and maintaining the magnitude of said positive pressure within the patient's airway at a value sufficient to prevent said episodes of airway obstruction during said sequence of inspiratory and expiratory phases.

* * * * *